(12) United States Patent
Myung et al.

(10) Patent No.: US 8,334,044 B2
(45) Date of Patent: Dec. 18, 2012

(54) HYDROGEL-METAL ASSEMBLY

(75) Inventors: David Myung, Santa Clara, CA (US);
Beinn V. O. Mulr, Palo Alto, CA (US);
Curtis W. Frank, Cupertino, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 663 days.

(21) Appl. No.: 12/069,186

(22) Filed: Feb. 6, 2008

(65) Prior Publication Data
US 2008/0241214 A1 Oct. 2, 2008

Related U.S. Application Data

(60) Provisional application No. 60/899,961, filed on Feb. 6, 2007.

(51) Int. Cl.
*A61F 2/02* (2006.01)
*B32B 15/04* (2006.01)
*B32B 27/24* (2006.01)
*B32B 33/00* (2006.01)

(52) U.S. Cl. ........ 428/141; 428/339; 428/420; 428/457; 623/11.11; 623/926

(58) Field of Classification Search .................. 428/457
See application file for complete search history.

(56) References Cited

U.S. PATENT DOCUMENTS

| | | |
|---|---|---|
| 5,314,478 A | 5/1994 | Oka et al. |
| 5,403,893 A | 4/1995 | Tanaka et al. |
| 6,120,904 A | 9/2000 | Hostettler et al. |
| 6,265,016 B1 | 7/2001 | Hostettler et al. |
| 6,372,815 B1 * | 4/2002 | Sulc et al. ..................... 523/106 |
| 6,629,997 B2 | 10/2003 | Mansmann |
| 7,066,958 B2 | 6/2006 | Ferree |
| 7,067,194 B2 | 6/2006 | Mao et al. |
| 7,204,897 B2 | 4/2007 | Stoy et al. |
| 2003/0008396 A1 * | 1/2003 | Ku ................................ 435/397 |
| 2003/0083389 A1 | 5/2003 | Kao et al. |
| 2004/0199250 A1 * | 10/2004 | Fell ............................. 623/14.12 |

(Continued)

OTHER PUBLICATIONS

J.P. Mtinlinna, L.V.J. Lassila, I.Kangasniemi, P.K. Vallittu, Isocyanato-and Methacryloxysilanes Promote Bis-GMA Adhesion to Ttanium, Sep. 29, 2003, 360-364, Turku, Finland.*

(Continued)

*Primary Examiner* — Ramsey Zacharia
(74) *Attorney, Agent, or Firm* — Lumen Patent Firm (57) ABSTRACT

A hydrogel-metal assembly is provided. An intervening polymer network is used to bond together a water-swollen hydrogel layer and a biocompatible surface-modified metallic layer. The hydrogel layer is a water-swollen hydrogel layer of at least two interpenetrating polymers. The surface of the biocompatible surface-modified metallic layer is surface-modified with an inorganic material. The intervening polymer network has been chemically grafted to the inorganic material of the biocompatible surface-modified metallic layer through bi-functional linker molecules. The intervening polymer network is further physically or chemically cross-linked with the polymers of the water-swollen hydrogel. The hydrogel-metal assembly can be adapted to form a medical device, medical implant, an artificial implant, an orthopedic implant, or at least as part of a joint. The hydrogel-metal assembly is attractive for use as such implants or devices due to its characteristics such as, for example, low coefficient of friction, impact-absorption capacity or strength, and/or biocompatibility.

9 Claims, 8 Drawing Sheets

U.S. PATENT DOCUMENTS

| | | |
|---|---|---|
| 2005/0287187 A1 | 12/2005 | Mansmann |
| 2006/0083773 A1 | 4/2006 | Myung et al. |
| 2006/0193899 A1 | 8/2006 | Sawhney |
| 2006/0224244 A1* | 10/2006 | Thomas et al. ............ 623/20.28 |
| 2006/0240478 A1 | 10/2006 | Nishimi et al. |

OTHER PUBLICATIONS

Yu-Song Pan, Dang-Sheng Xiong, Ru-Yin Ma, "A study on the fiction properties of poly (vinyl alcohol) hydrogel as articular cartiliage against titanium alloy", Mar. 24, 2006, pp. 1021-1025 Wear 262 (2007), Nan Jing 210094, China.

J.P. Matinlinna, L.V.J. Lassila, I.Kangasniemi, P.K. Vallittu, Isocyanato- and Methacryloxysilanes Promote Bis-GMA Adhesion to Titanium, Sep. 29, 2003, 360-364, Turku, Finland.

A.Simon,T.Cohem-Bouhacina, M.C Porte, J.P. Aime,C.Baquey, Study of to Grafting Methods for Pbtaining a 3-Aminopyltiethoxysilane Monolayer on Silica Surfac, Nov. 13, 2001, 278-283, Jornal of Colloid and Interface Science 251 (2002) Bordeaux Cedex, France.

A.Nanci,J.D Wuest,L.Peru,P.Brunet,V.Sharma, S.Zalzal, M.D. McKee, Chemical modification of titanium surface for covalent attached of biological molecules, Nov. 21, 1996, 324-335,1198 John Wiley & Sons, Inc. Station Centre-Ville, Montereal QC.

Alexander Revizin, Ryan J. Russell, Vamsi K. Yadavalli, Won-Gun Koh, Curt Deister, David D. Hile, Michael B. Mellott, Michael V. Pishko, Fabrication of Poly (ethylene glycol) Hydrogel Microstructures Using Photolithography, Jan. 12, 2001.

Daisaku Kaneko, Tomohiro Tada, Takayuki Kurokawa, Jian P. Gong, Yoshihito Osada, Mechanically Strong Hydrogels with Ultra-Low Frictional Coefficients, Apr. 27, 2004, 535-538, Sapporo, Japan.

Shou-Jun Xiao, Marcus Textor, Nicholas D. Spencer, Covalent Attachment of Cell-Adhesive (Arg-Gly, Asp) Containing Peptides to Titanium Surface, Mar. 3, 1998, 5507-5516, Langmuir 1998, Zurich, Switzerland.

Go Kagata, Jian Ping, Yoshihito Osada, Friction of Gels.6. Effects of Sliding Viscoelastic Responses of the Network, Jun. 21, 2001, 4596-4601, J. Phys Chem B 2002, Supporo, Japan.

* cited by examiner

HYDROGEL-METAL ASSEMBLY

CROSS-REFERENCE TO RELATED APPLICATIONS

This application claims priority from U.S. provisional patent application No. 60/899,961 filed Feb. 6, 2007, which is incorporated herein by reference.

FIELD OF THE INVENTION

The present invention relates generally to medical devices. More particularly, the present invention relates to hydrogel-metal assemblies for biomedical devices and implants.

BACKGROUND OF THE INVENTION

The performance of many implanted biomedical devices is dependent on the surface characteristics of the implant material. Hydrogel coatings are now being developed and used by investigators to lower the thrombogenicity and immunogenicity of these devices, phenomena that are usually initiated by the adsorption of body fluid proteins on the implant. Improvement of tribological properties is also important in orthopedic devices, almost all of which involve sliding articulations between two surfaces. For example, an artificial joint often involves the combination of metal and plastic. In a total knee replacement, a metal component is attached to the femur, which, upon flexion, glides over a plastic bearing connected to a metal base that is attached to the top of the tibia. Artificial vertebral discs available for human use today involve variations of metal-on-plastic or plastic-on-plastic gliding articulations between components sandwiched between two vertebrae. A total hip replacement device usually contains a metallic implant with a "ball" on its end that sits within a shell implanted inside the pelvic "socket" (the acetabulum). There are also similar prostheses used to partially (i.e. hemi-arthroplasty) or totally (i.e. total arthroplasty) replace or resurface other joints such as the shoulder and ankle and the joints in the hands and feet. In prosthetic joint applications, the most commonly used metals are titanium and cobalt chrome while the most commonly used plastic is polyethylene. Unfortunately, the use of plastics in orthopedic prostheses has several disadvantages, including rigidity, wear, and low biocompatibility compared to biological solutions. Other materials such as ceramics are now being developed and used in these devices as alternative bearing materials to metals and polymers. Accordingly, there is a need in the art to develop new materials for orthopedic and medical devices that would at least overcome some of these disadvantages. The present invention addresses these needs and provides devices based on hydrogel-metal assemblies.

SUMMARY OF THE INVENTION

Figure 1:
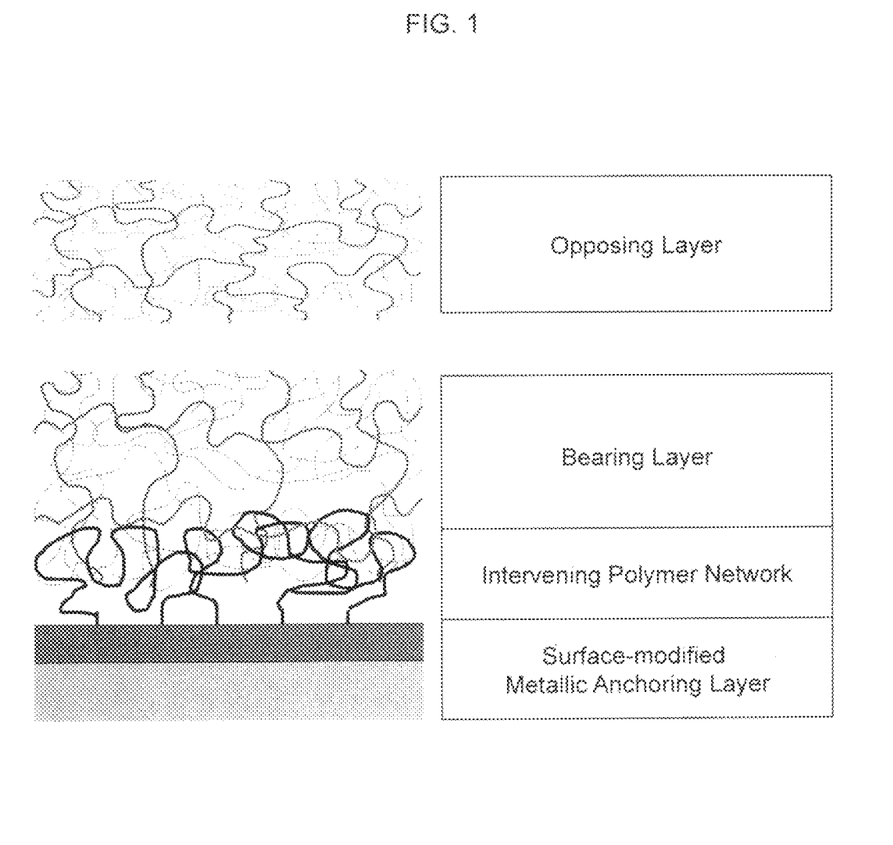

The present invention provides a hydrogel-metal assembly. An intervening polymer network is used to bond together a water-swollen hydrogel layer (bearing layer) and a biocompatible surface-modified metallic layer (also referred to as a surface-modified metallic anchoring layer) (FIG. 1). The hydrogel layer is a water-swollen hydrogel layer of at least two interpenetrating polymers. At least one of these polymers is a hydrophilic polymer. In a preferred embodiment, the polymers of the hydrogel layer are different types of polymers, and at least one of these polymers is chemically cross-linked. The surface of the biocompatible surface-modified metallic layer is surface-modified with an inorganic material. The intervening polymer network has been chemically grafted to the inorganic material of the biocompatible surface-modified metallic layer through bi-functional linker molecules. The intervening polymer network is further physically or chemically cross-linked with the polymers of the water-swollen hydrogel.

The hydrogel-metal assembly can be adapted to form a medical device, medical implant, an artificial implant, an orthopedic implant, or at least as part of a joint. The hydrogel-metal assembly can also include an opposing layer (FIG. 1). The surface of the opposing layer could face the surface of the hydrogel layer, and the two facing layers could be adapted to form a medical device, medical implant, an artificial implant, an orthopedic implant, or at least as part of a joint. The surface of the opposing layer could be metal, bone, ceramic, cartilage, a polymer, a hydrogel, or a water-swollen hydrogel of at least two interpenetrating polymers. In an example of an artificial joint application, the hydrogel portion of the hydrogel-metal assembly could articulate either with itself or another hydrogel (gel-on-gel), with another synthetic material (gel-on-polymer, metal, or ceramic), or with natural cartilage (gel-on-cartilage) on an opposing surface. For example, the hydrogel can articulate with a patient's existing natural cartilage, or it can articulate with the polymer, metal, or ceramic in an opposing joint prosthesis. In either case, the hydrogel-metal implant would be placed with the metal component contacting the underlying bone to enable the hydrogel component to create a lubricious joint interface.

In a preferred embodiment, the hydrogel-metal assembly could have, either by itself or in any of its combinations, the following characteristics: (i) a hydrogel layer with a maximum thickness of at least 0.5 mm, (ii) a hydrogel layer containing a fluid of at least 15% and up to 95% of the volume of the hydrogel layer, (iii) a hydrogel layer with at least one of the polymers having a charge (i.e. negative or positive charge), (iv) a hydrogel layer with a surface coefficient of friction of less than 0.2, (v) a biocompatible surface-modified metallic anchoring layer whereby the surface has a roughness of over 500 nm, (vi) a hydrogel-metal assembly with a shear strength of at least 30 kPa, and (vii) an intervening polymer network that assembles the hydrogel layer to the surface-modified metallic anchoring layer.

At least some of these characteristics allow the hydrogel-metal assembly to be advantageous over conventional orthopedic implants or medical devices. For example, the hydrogel-metal assembly is attractive for use as orthopedic implants or medical devices due to its characteristics such as, for example, low coefficient of friction, impact-absorption capacity or strength, and/or biocompatibility.

BRIEF DESCRIPTION OF THE FIGURES

The present invention together with its objectives and advantages will be understood by reading the following description in conjunction with the drawings, in which:

FIG. 1 shows a schematic of a hydrogel-metal assembly with different layers according to an embodiment of the present invention. The left part of the figure illustrates the corresponding layers or elements shown on the right part of the figure. The relatively darker and thicker lines in the left part of the figure indicate an intervening polymer network. The two relatively thinner and lighter lines in the left part of the figure indicate an interpenetrating polymer network hydrogel composed of two polymers and forming the bearing layer or in one example an opposing layer. The intervening polymer network could be chemically grafted to the biocompatible metallic anchoring layer through bi-functional linker molecules, and the intervening polymer network could be physically or chemically cross-linked with the polymers of the bearing layer.

(A) shows according to the present invention a semi-interpenetrating network in which one of the networks acts as the anchoring intervening polymer. Telechelic macromonomers (dark lines) and linear polymers (gray lines) are mixed together in solution and cast over a titanium/$SiO_2$ surface that is functionalized with UV-sensitive crosslinkable groups (small circles). Exposure to UV light in the presence of a photoinitiator leads to free-radical polymerization and crosslinking of these crosslinkable groups on both the telechelic macromonomers and the $SiO_2$ surface. The result of free-radical polymerization and crosslinking is shown on the right. The ends of the telechelic macromonomers (dark lines) have copolymerized and bonded with the surface of the $SiO_2$. The linear polymers (grey lines) are physically trapped within this first network, forming a second, physically crosslinked network interpenetrating the first chemically crosslinked network.

(B) shows according to the present invention a fully interpenetrating network in which an additional polymer acts as the anchoring intervening polymer. A pre-existing interpenetrating polymer network (thin and thick grey lines) is placed over a titanium/$SiO_2$ surface that is functionalized with UV-sensitive crosslinkable groups (small circles). At the interface between the hydrogel and surface-modified metal is a precursor solution of reactive monomers (grey circles). These monomers partially penetrate the matrix of the overlying interpenetrating polymer network. Upon exposure to UV, the monomers polymerize and crosslink to the surface-modified titanium, yielding an intervening polymer network (dark thick lines) that is bonded to the underling surface and entangled with the overlying hydrogel.

(C) shows according to the present invention a fully interpenetrating network in which one of the networks is interfacially copolymerized with an anchoring intervening polymer network. A pre-existing homopolymer network (thin lines) are placed over a titanium/$SiO_2$ surface that is functionalized with UV-sensitive crosslinkable groups (small circles). The homopolymer network is swollen with the precursor monomers of a second network (grey circles). At the interface between the monomer-swollen hydrogel and the surface-modified metal is a precursor solution of another reactive monomer (black circles). These monomers partially penetrate the matrix of the overlying interpenetrating polymer network. Upon exposure to UV, the monomers co-polymerize, with the monomers at the interface crosslinking to the surface-modified titanium, yielding an intervening polymer network that is bonded to the underling surface and entangled with the overlying hydrogel.

DETAILED DESCRIPTION

In the preferred embodiment of the present invention, an interpenetrating polymer network (IPN) water-swollen hydrogel is adhered via an intervening polymer network that is itself bonded to a surface-modified metal (e.g. titanium metal or cobalt-chrome alloy). The metal is modified on its surface with an embedded layer of inorganic material such as $SiO_2$ or hydroxyapatite formed by grit-blasting. End-functionalized chemical linkers are then reacted to the inorganic material via silanol or phosphate bonds on one end. The free-ends of the linkers are then available for reaction and/or interaction with the intervening polymer. The intervening polymer can be a preformed polymer (e.g. a macromonomer or an oligomer) that can be coupled to the surface of the modified metal, or be grown from monomers and crosslinked=through a polymerization reaction. When the coupling or polymerization of the intervening polymer is done in the presence of the IPN hydrogel, the intervening polymer is chemically linked to the modified metal and forms permanent entanglements and, in some cases, covalent bonds with the IPN. The degree and depth to which the intervening polymer network is entangled with the IPN hydrogel is determined by the time allowed for the intervening polymer network precursor solution to diffuse into the IPN hydrogel. Diffusion times are proportional to the molecular weight of the intervening polymer network precursor and are also dependent on its relative hydrophilicity and hydrophobicity.

For the purposes of this invention, the interpenetrating polymer network hydrogel can be composed of any two polymers, wherein at least one of the polymers is hydrophilic. For example, a hydrophilic linear, telechelic, or end-functionalized macromonomer may be used to form one of the networks in the interpenetrating polymer network. Examples of macromonomers include, but are not limited to, poly(ethylene glycol), poly(acrylic acid), poly(N-vinyl pyrrolidone), polycarbonate, poly(vinyl alcohol), poly(dimethylsulfoxide), polyurethane, polymethylmethacrylate, and biomacromolecules such as chitosan, dextran, and hyaluronic acid. Derivatives and combinations of these macromonomers and biomacromolecules can be used. End-group or side-group functionalities to these macromolecules and biomacromolecules may include, but are not limited to, acrylate (e.g. PEG-diacrylate), methacrylate, vinyl, allyl, N-vinyl sulfones, methacrylamide (e.g. PEG-diacrylamide), and acrylamide (e.g. PEG-diacrylamide).

A variety of vinyl-based monomers may be polymerized and crosslinked to form one of the networks, such as acrylic acid, acrylamide, methacrylamide, N-hydroxyethyl acrylamide, N-isopropylacrylamide, methacrylic acid, 2-acrylamido-2-methylpropanesulfonic acid, methylmethacrylate, dimethylsulfoxide, N-vinyl pyrrolidone, 2-hydroxyethyl methacrylate, 2-hydroxyethyl acrylate or derivatives thereof. Any type of compatible cross-linkers may be used such as for example ethylene glycol dimethacrylate, ethylene glycol diacrylate, diethylene glycol dimethacrylate (or diacrylate), triethylene glycol dimethacrylate (or diacrylate), tetraethylene glycol dimethacrylate (or diacrylate), polyethylene glycol dimethacrylate, or polyethylene glycol diacrylate, methylene bisacrylamide, N,N'-(1,2-dihydroxyethylene)bisacrylamide, derivatives, or combinations thereof. Any number of photoinitiators can also be used. These include, but are not limited to, 2-hydroxy-2-methyl-propiophenone and 2-hydroxy-1-[4-(2-hydroxyethoxy)phenyl]-2-methyl-1-propanone.

Any of the aforementioned polymers, their derivatives, or combinations thereof, can be used to comprise additional interpenetrating polymer networks to create IPNs with more than two component networks.

Intervening polymer networks (for anchoring the hydrogel to the surface-modified metal) may include, but are not limited to, any of the aforementioned polymers used to create the IPN hydrogel, as well as any monomer-based polymers, functionalized oligomers and macromonomers, branched and functionalized macromonomers, dendrimers, and reactive, end-functionalized dendrimers. Examples of monomer-based polymers are poly(hydroxyethyl methacrylate), poly(hydroxyethyl acrylate), poly(acrylamide), poly(acrylic acid), and poly(methacrylic acid). Examples of oligomers and macromonomers are PEG-diacrylate, PEG-dimethacrylate, PEG-diacrylamide, PEG-diallylether, poly(vinyl alcohol), and crosslinkable, functionalized biomacromolecules like chitosan and hyaluronic acid. Examples of branched macromonomers are end-functionalized four-arm poly(ethylene glycol) with acrylate, methacrylate, allyl, vinyl, acrylamide or methacrylamide moieties or other crosslinkable or adhesion-promoting functional groups that promote adhesion via non-covalent interactions. Examples of chemical moieties that promote non-covalent adhesion are acidic end groups that either create hydrogen bonds (e.g. 3-hydroxytyramine) or acidic, negatively charged carboxylate and sulfonate groups that can complex with divalent cations (e.g. calcium, zinc, or magnesium) to form ion bridges. An example of a dendrimer is a ethylenediamine-core poly (amidoamine) [PAMAM] dendrimer, with or without end-functionalization with polymerizable or reactive end groups.

In a preferred embodiment for the bonding process between hydrogel and metal components, the hydrogel is bonded to the titanium by the following process: (1) a layer of $SiO_2$ is embedded within the titanium surface by grit-blasting with $SiO_2$-coated aluminum particles, (2) a hetero-bifunctional chemical is deposited and reacted with the $SiO_2$ to form Si—O—Si bonds on the surface of the $SiO_2$, and (3) vinyl-containing (e.g. vinyl, acrylate, methacrylate, acrylamide, methacrylamide, or allyl) monomers and/or macromonomers are cast over and copolymerized with the functional groups on the $SiO_2$-coated titanium by UV-initiated free radical polymerization. Any number of heterobifunctional linkers that are commonly used to functionalize $SiO_2$ substrates can be used in Step (2), such as 3-(trimethoxysilyl)propyl acrylate, 3-(triethoxysilyl)propyl methacrylate (or acrylate), and/or 3-(trichlorosilyl)propyl methacrylate (or acrylate). The heterobifunctional chemical 3-isocyanatopropyltrimethoxysilane can be used. Aminopropyltriethoxysilane (APTES) can also be linked to the $SiO_2$ surface, followed by reaction with an activated acid such as acryloyl chloride or methacryloyl chloride, to yield photopolymerizable groups on the surface. Finally, the surface of titanium can be modified directly by oxidizing the titanium surface through a plasma cleaning process or by a "piranha" etching process, followed by reaction with a heterbifunctional compound such as 3-(trimethoxysilyl)propyl methacrylate or APTES.

In addition to those described above, the bifunctional linkers used to tether the intervening polymer network to an inorganic surface may include any derivative of alkoxy-silanes (methoxy and ethoxy functionalized silanes), and chloro-silanes. The bifunctional linkers can contain one or more of these silane groups on one end in conjunction with any number of functional groups on the other end, listed below:

| Functional Group | Type of reaction |
| --- | --- |
| Acrylate | Free radical polymerization |
| Methacrylate | Free radical polymerization |
| Acrylamide | Free radical polymerization |
| Isocyanate | Reaction with ROH -> urethane |
| Styrene | Free radical polymerization |
| Epoxide | Ring-opening |
| Alkene (allyl, vinyl) | Free radical polymerization |
| Amine | Ring opening or esterification |
| Alkyl halide | Reaction via nucleophilic attack |
| Thiol | Sulfhydryl reactions |
| Phenol | Hydrogen bonding |
| Carboxylate/Sulfonate | Complexation (e.g. hydrogen bonding or divalent cations) |

Trimethoxysilanes include, but are not limited to, 3-(trimethoxysilyl)propyl methacrylate, N-[3-(trimethoxysilyl)propyl]aniline, trimethoxy[2-(7-oxabicyclo[4.1.0]hept-3-yl)ethyl]silane, trimethoxy[3-(methylamino)propyl]silane, trimethoxy(7-octen-1-yl)silane, trimethoxy(vinyl)silane, allyltrimethoxysilane, 3-[2-(2-aminoethylamino)ethylamino]propyl-trimethoxysilane, [3-(2-aminoethylamino)propyl]tri-methoxysilane, (3-aminopropyl)trimethoxysilane, (3-bromopropyl)trimethoxysilane, (3-chloropropyl)trimethoxysilane, (3-glycidyloxypropyl)trimethoxysilane, (3-iodopropyl)trimethoxysilane, (3-mercaptopropyl)trimethoxysilane, 3-(trimethoxysilyl)propyl acrylate, 1-[3-(trimethoxysilyl)propyl]urea, N-[3-(trimethoxysilyl)propyl]-N'-(4-vinylbenzyl)ethylenediamine hydrochloride.

Triethoxysilanes may include, but not limited to, (3-aminopropyl)triethoxysilane, poly(hydroxyethylmethacrylate), triethoxy(3-isocyanatopropyl)silane, triethoxy(4-methoxyphenyl)silane, triethoxyvinylsilane, Allyltriethoxysilane, 3-cyanopropyltriethoxysilane, (3-mercaptopropyl)triethoxysilane, 3-(triethoxysilyl)propionitrile.

Trichlorosilanes may include, but not limited to, 3-cyanopropyltrichlorosilane, trichloro(2-cyanoethyl)silane, trichloro(3-chloropropyl)silane, trichloro(4-chlorophenyl)silane, trichlorovinylsilane, allyltrichlorosilane, (3 bromopropyl)trichlorosilane, 3-cyanopropyltrichlorosilane, octenyltrichlorosilane, 3-(trichlorosilyl)propyl methacrylate.

Mixed silanes (containing alkyl-silane functionalization and either alkoxy or halogen functionalized silane) may include, but not limited to, diethoxy(methyl)vinylsilane, dimethoxymethylvinylsilane, ethoxy(dimethyl)vinylsilane, 3-(2-aminoethylamino)propyl-dimethoxymethylsilane, 3-aminopropyl(diethoxy)methylsilane, diethoxy(3-glycidyloxypropyl)methylsilane, 3-(diethoxymethylsilyl)propyl methacrylate, 3-(dimethoxymethylsilyl)-1-propanethiol, 3-glycidoxypropyldimethoxymethylsilane, 3-glycidoxypropyldimethylethoxysilane. Other bifunctional linkers include those containing azide, carbene, benzophenone, isocyanate, sulhydryl, thiol, maleimide, succinimide functional groups in addition to silane moieties.

Other types of linkers may include PAMAM dendrimers that contain trimethoxysilyl surface groups. These are PAMAM dendrimers with an ethylenediamine core, of generation 1 to 7. An example of this multifunctional linker is the PAMAM-OS-trimethoxysilyl dendrimer of generation 4.

EXAMPLE

The following is an exemplary description of experimental methodology and results performed by the inventors and is presented without limiting the scope of the invention.

Experimental Methodology

Materials

Titanium plates (99% pure), each with an area of 6.5 cm$^2$ and a thickness of 1 mm, were obtained from Alfa Aesar (Ward Hill, Mass.). The different sizes of PEG used for the experiment were distinguished on the basis of the molecular weight (MW) of the PEG macromonomer. PEG(X) designates a PEG macromonomer of molecular weight X in Daltons. PEG(1000)-dimethacrylate was obtained from Polysciences (Warrington, Pa.), while PEG(4600), acrylic acid (AA), 2-hydroxyethylmethacrylate (HEMA), triethylene glycol dimethacrylate, and 2-hydroxy-2-methyl-propiophenone were obtained from Sigma-Aldrich (St. Louis, Mo.). 3-(trimethoxysilyl)propyl methacrylate (TMSPM) (3M ESPE "Sil" reagent) was used for silane coupling and was obtained from 3M (St. Paul, Minn.). The Rocatec Jr. Blasting module and SiO$_2$-coated aluminum oxide sand particles were obtained from 3M (St. Paul, Minn.).

Titanium Modification

Titanium samples were grit-blasted using the Rocatec Junior Bonding system. The titanium surfaces were blasted with SiO$_2$-coated alumina particles (~110 µm in diameter) with a pressure of 2.8 bar at a distance of 1 cm for an average time of 5 seconds per square millimeter of blast area. Apart from "ceramicising" the surface of titanium, the impact of the particles also causes a certain amount of roughening. Ceramization of the blasted surface takes place when the grains hit the surface creating a so-called "triboplasma". The SiO$_2$ is impregnated into the surface up to a depth of 15 µm and at the same time is fused to the surface in islands. The high level of energy is created by the acceleration of the particles to a velocity of up to 1000 km/h within the blast nozzle.

To serve as a basis for comparison for the grit-blasted surfaces, titanium was also modified with SiO$_2$ by a vapor deposition process to yield coated surfaces that were not roughened. A silicon dioxide film was deposited on the titanium using a low temperature plasma enhanced chemical vapor deposition (PECVD) system (Surface Technology Systems (STS) plc, Newport, UK), at a deposition rate of 35 nm/min, carried out in high frequency mode at 40 W, 650 mTorr and 350° C., using 2% silane (in argon carrier gas) and nitrous oxide as precursors. Film thickness, based on deposition on a silicon control wafer, was determined to be 114 nm using single wavelength fixed angle ellipsometry using a Rudolph Research AutoEL III Ellipsometer (Rudolph Technologies Inc., New Jersey, USA) equipped with a 632.8 nm HeNe 0.2 mW class II laser set at an angle of 70°. The refractive index of the film was determined to be 1.47.

Silane Coupling to Ceramicized Titanium

The SiO$_2$-coated titanium is chemically modified by drop-casting a solution of 3-(trimethoxysilyl)propyl methacrylate (TMSPM) in ethanol (Bind Silane, 3M), a hetero-bifunctional linker, onto its surface, allowing the solvent to evaporate and the linker to react for five minutes. This creates a linkage between the silane group and the SiO$_2$ surface, leaving the methacrylate groups free to react with other methacrylate or acrylate-containing monomers or macromonomers.

Bonding of Hydrogel Polymers to Titanium

In this invention, a hydrogel polymer is attached to a surface-modified metal through an intervening polymer network that interpenetrates the hydrogel polymer and is chemically bonded to the surface-modified metal. The basis of the bonding is the simultaneous occurrence of (1) interdiffusion and entanglement with the overlying hydrogel matrix and (2) chemical linkage to inorganic material embedded in the surface of metal. For this bonding to be successful, the intervening polymer network precursors must be sufficiently soluble in water that it can diffuse into the aqueous hydrogel matrix while being capable of polymerizing with the functional groups on the modified metal surface.

In these experiments, PEG(1000) single networks, PEG/PAA semi-interpenetrating networks or PHEMA single networks were bonded to titanium plates. The tribochemical process used for bonding the hydrogel and titanium components proceeds as follows: (1) a layer of SiO$_2$ is embedded within the titanium surface by grit-blasting with SiO$_2$-coated aluminum particles, (2) the hetero-bifunctional coupling agent 3-(trimethoxysilyl)propyl methacrylate is deposited and reacted with the SiO$_2$ to form Si—O—Si bonds on the surface of the SiO$_2$, and (3) acrylate and/or methacrylate-containing monomers and/or macromonomers are cast over and copolymerized with the methacrylate groups on the SiO$_2$-coated titanium by UV-initiated free radical polymerization.

Hydrogel Grafting

Figure 2:
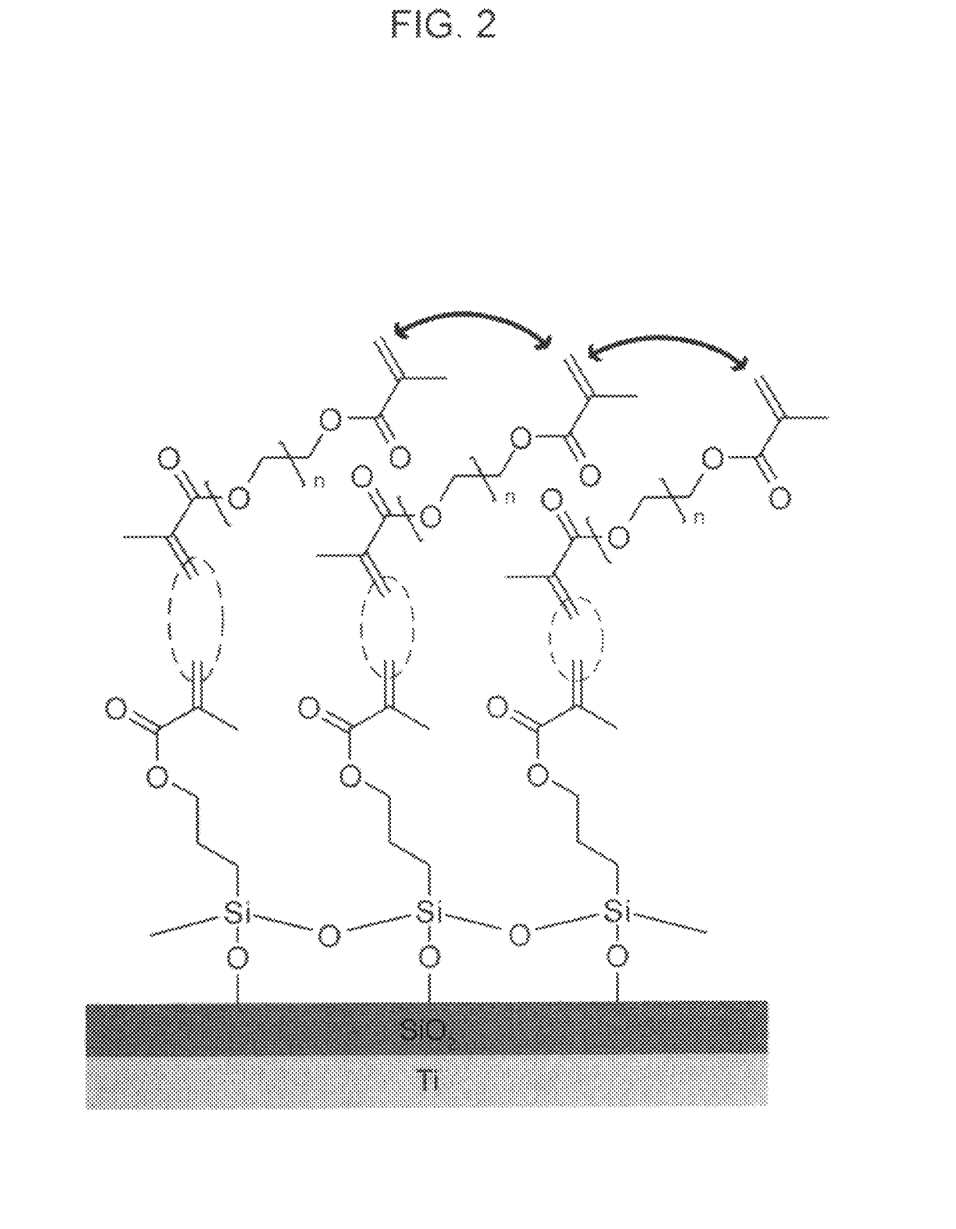
FIG. 2 shows according to an embodiment of the present invention that 3-(trimethoxysilyl)propyl methacrylate (TM-SPM) molecules tethered to $Ti/SiO_2$ can make further covalent linkages via free-radical polymerization with methacrylate-containing molecules (within dotted ellipses), such as poly(ethylene glycol) dimethacrylate macromonomers (PEG-DMA, top). The PEG-DMA molecules can also be covalently linked with each other (black arrows).

The chemical reaction in which the telechelic PEG macromonomers are attached to titanium surfaces is shown in FIG. 2. In the presence of methacrylate-functionalized PEG macromonomers (right), two types of chemical linkages can be made: (1) between the surface linker and the PEG macromonomer (lower arrows), and (2) between PEG macromonomers (upper arrows). In this way, hydrogels were chemically bonded to the surface of titanium plates. Other polymerizable, vinyl-containing functional groups may be used in place of the methacrylate groups.

Profilometry

Profilometry was carried out using a Dektak 150 Surface Profiler (Veeco Instruments Inc., Tucson, Ariz.) using a B-type (red) stylus with a 12.5 µm tip diameter. Two-dimensional profiles were measured using a 2 mm scan length with a duration of 60 s (33 µm/s), resulting in a resolution of 111 nm/sample. The binning range was set to 65.5 µm with a stylus force of 10 mg (as recommended for hard surfaces). All samples were leveled (to remove sample tilt) before roughness calculation using Dektak V9 Software.

Contact Angle Measurements

Contact angle measurements were taken using a FTÅ200 contact angle apparatus with a motorized syringe pump (First Ten Ångstroms, Portsmouth, Va.). Image capture used a Sanyo camera with supplied FTÅ200 video software V1.98 (AccuSoft Corp., Northborough, Mass.). Standard drop size was 6 µL (syringe operating at 0.3 µL/s and ~20 s per drop).

Scanning Electron Microscopy (SEM)

Prior to scanning electron microscopy observation, all samples were mounted onto Al stubs using Electrodag 502 (Ted Pella, Inc., Redding, Calif.) conductive carbon adhesive. Samples were then sputter coated using a Cressington 108 auto DC magnetron sputter coater with planetary motion tilting rotary stage (Watford, England), with a 1-2 nm of $Au_{60}Pd_{40}$ alloy, at a current of 20 mA for 45 s under a low pressure (0.08 mbar) Ar atmosphere. This coating was applied in order to increase surface electrical conductivity.

Scanning electron microscopy was carried out using a FEI XL Sirion SEM (FEI Company, Hillsboro, Oreg.) using a FEG source operating at an acceleration voltage of 5 kV, with spot size 3, under high vacuum. Low magnification images (100× to 10000×) were collected using a standard secondary electron detector. High magnification images (>10000×) were collected with an in-lens SE detector in TLD mode. Images are presented as obtained without modification.

Energy Dispersive X-Ray Spectroscopy (EDX)

Energy-dispersive X-ray spectroscopy (EDS) analysis and EDS compositional maps were obtained using an EDAX microanalysis module (EDAX, Mahwah, N.J.) at an accelerating voltage of 15 kV. Each compositional map consists of approximately 100 frames using a dwell time of 200 µs, and was collected using EDAX Genesis analysis software V4.61.

Lap-Shear Adhesion Tests

The strength of hydrogel-titanium bonds was tested using lap-shear adhesion experiments (ASTM D3163) in which two titanium plates were bonded together using a 250 µm thick hydrogel layer and pulled apart using an Instron 5844 materials testing apparatus equipped with a 1 kN load cell (Instron Corp, Norwood, Mass.). Adhesion to both surface-modified titanium (via tribochemical silyl-methacrylate linkage) and unmodified titanium surfaces was tested. In addition, three different hydro gels were tested: (1) a PEG-DMA macromonomer (MW 1000), (2) a crosslinked PHEMA single network, and (3) a PEG/PAA semi-interpenetrating network (PEG MW 4600), all of which would be expected to form bonds with the methacrylate groups on the modified titanium surface. Hydrogel precursor solutions were injected between staggered titanium plates and exposed to UV light. The staggered, adherent plates were soaked in phosphate buffered saline (pH 7.4) overnight prior to testing. The lap-shear experiments involved gripping the free end of the titanium plates and then pulling them in opposite directions, while collecting both load and extension data.

Experimental Results

Grit-Blasting of Titanium

Figure 3:
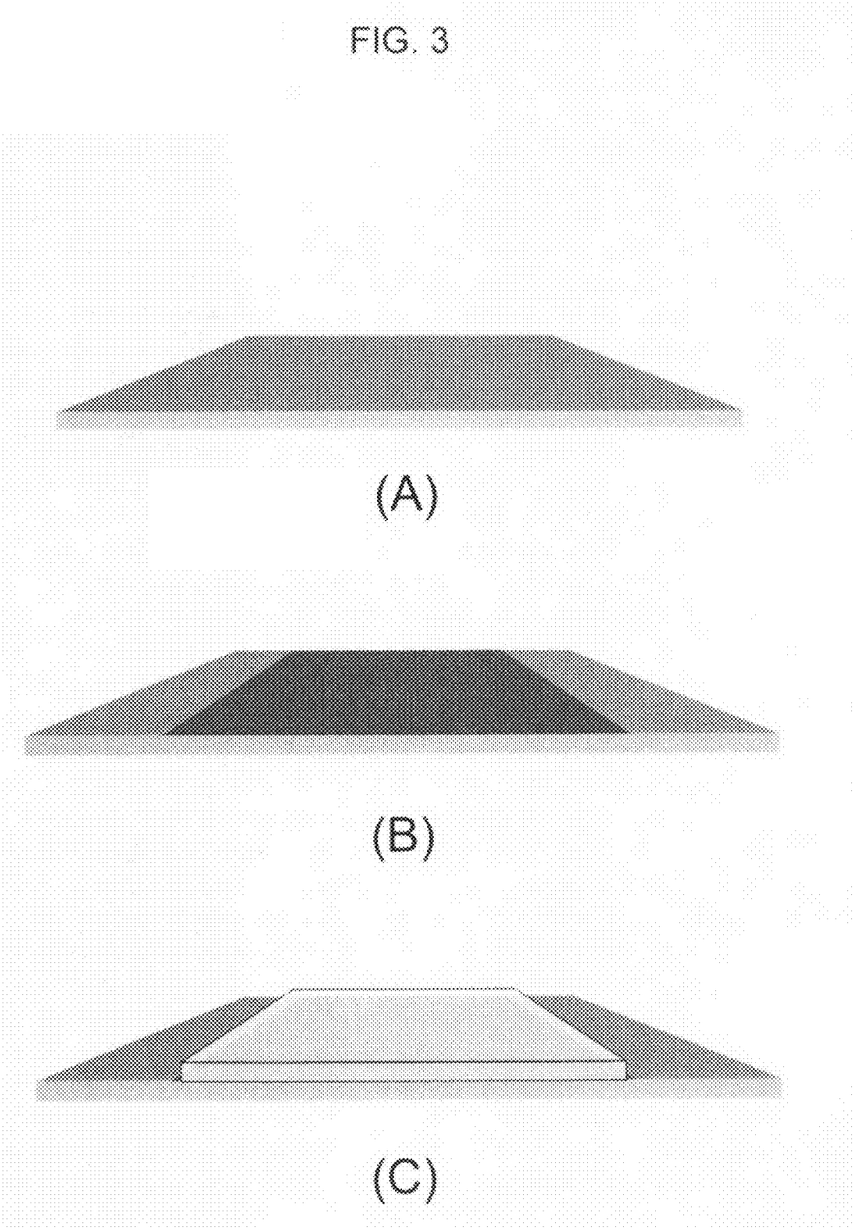
FIG. 3 illustrates process of forming a hydrogel-metal assembly according to to an embodiment of the present invention. (A) shows a metal (e.g. titanium) substrate. (B) shows the metal plate after having been grit-blasted with aluminum oxide particles (e.g. 110 µm in diameter) coated with $SiO_2$, a process which roughens and impregnates the metal surface with a layer (dark region) of $SiO_2$. (C) shows a hydrogel grafted to the surface of the $SiO_2$-impregnated area of the metal.
Figure 4:
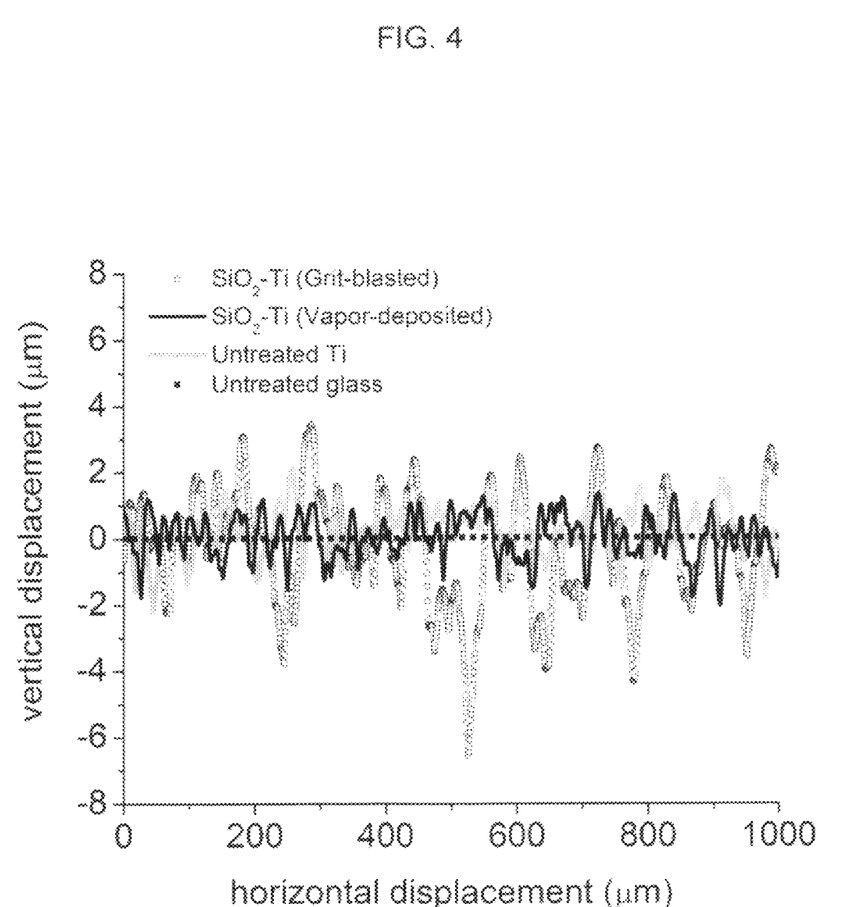
FIG. 4 shows according to an embodiment of the present invention an example of profilometry measurements performed on untreated and $SiO_2$-coated titanium substrates as well as untreated glass.

Titanium plates were grit-blasted using $SiO_2$-coated aluminum oxide particles and grafted to hydrogels, as depicted in FIG. 3. FIG. 4 shows profilometry data on the roughness of the grit-blasted region of the titania, compared with unroughened titania and glass that were measured as obtained (samples were cleaned with ethanol prior to analysis to remove any oils or debris). The grit-blasted titanium had the highest average roughness (over 1700 nm), which was over three times that measured for both the coated and uncoated titanium (~500 nm). Untreated glass had a roughness on the order of 6 nm. SEM analyses of the grit-blasted and unblasted surfaces (FIGS. 5-6) showed that the titanium surfaces that were directly treated were successfully impregnated with $SiO_2$, indicated by grayscale contrast between the blasted, FIG. 5(A), and unblasted, FIG. 5(B), regions, where the contrast is due to the build up of electrical charge within the insulating $SiO_2$ layer.

Figure 5:
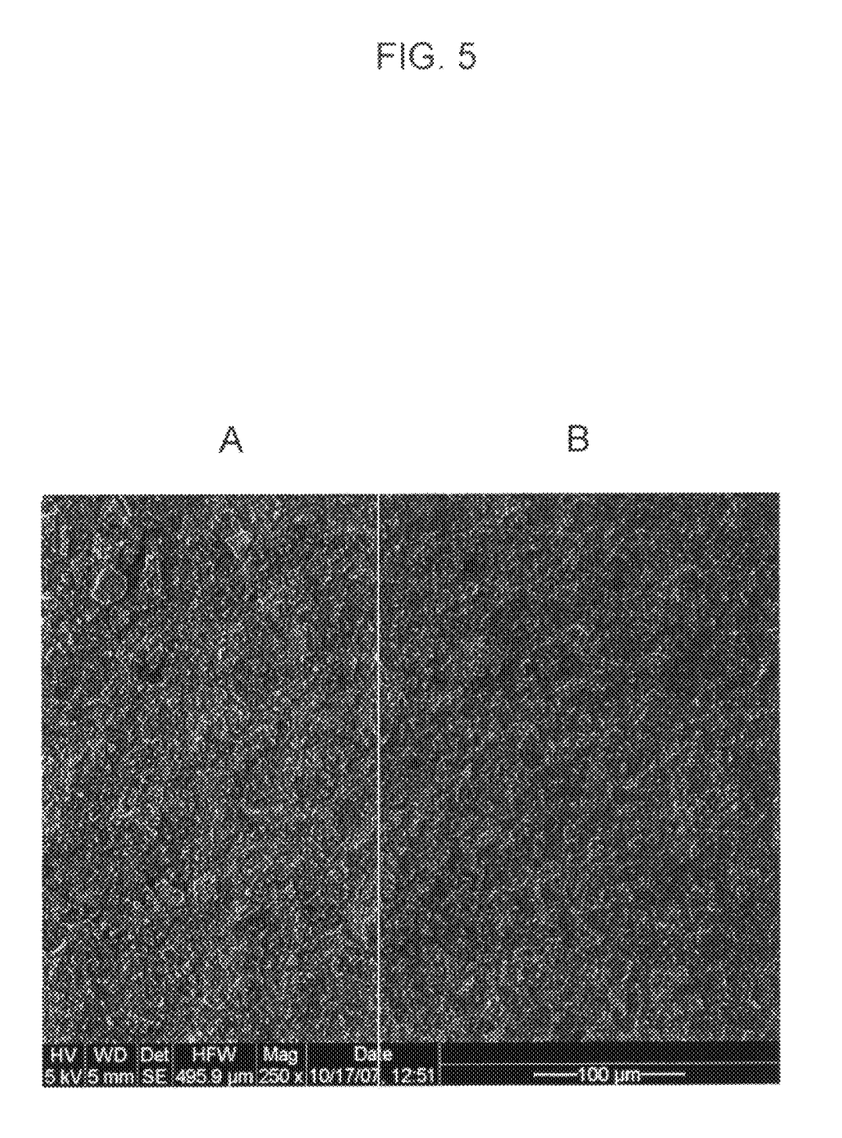
FIG. 5 shows according to an embodiment of the present invention a scanning electron microscope (SEM) image of a titanium surface with both $SiO_2$-modified (A) and unmodified (B) regions. The lighter region on the left (A) is the directly grit-blasted surface while the darker region on the right (B) is the unblasted titanium. The white/grey line is intended to guide the eyes of the reader along the border between the two regions.

At high magnification the $SiO_2$ appears as a densely packed, discrete white particulate material. At the same time, some residual $SiO_2$ appeared to have contaminated the unblasted region, presumably due to "collateral damage" caused by the blasting process, while unmodified titanium regions appear dark grey in the SEM image.

Composition mapping through energy dispersive x-ray spectroscopy was used to determine the atomic composition of the grit-blasted surface. However, the EDX composition map clearly showed that the grit-blasted regions are heterogeneous, with roughly equal distributions of $SiO_2$, $Al_2O_3$, and residual titanium metal.

Surface Chemistry

Table 1 summarizes the various surfaces prepared, their average roughness, followed by the post-treatment used (plasma cleaning or no plasma cleaning), the surface chemistry used (silanization or no silanization), the water contact angle of the surface, and the result of hydrogel grafting after overnight immersion in water.

TABLE 1

Measured parameters for untreated and $SiO_2$-modified titanium substrates as well as untreated glass.

| | Initial Treatment | Roughness (nm) | Post-Treatment | Surface Chemistry | Contact Angle (°) | Hydrogel Graft |
|---|---|---|---|---|---|---|
| Titanium | $SiO_2$ grit-blasting | 1708.1 ± 254.4 | none | TMSPM** | 14 ± 2 | Strongly bonded |
| | $SiO_2$ brit-blasting | | none | none | 7 ± 2 | Delaminated |
| | $SiO_2$ PECVD* | 522 ± 27.8 | plasma | TMSPM** | 53 ± 4 | Delaminated |
| | $SiO_2$ PECVD* | | plasma | none | 2 ± 1 | — |
| | none | 560.9 ± 13.8 | plasma | TMSPM** | 82 ± 2 | Delaminated |
| | none | | plasma | none | 2 ± 1 | Delaminated |
| | none | | none | TMSPM** | 99 ± 2 | Delaminated |
| | none | | none | none | 98 ± 6 | — |
| Glass | none | 6.7 ± 2.1 | plasma | TMSPM** | 64 ± 3 | Delaminated |
| | none | | plasma | none | 5 ± 1 | — |

*PECVD = plasma enhanced chemical vapour deposition
**TMSPM = 3-(trimethoxysilyl)propyl methacrylate Plasma treatment and/or silane-coupling of the samples were confirmed by a change in the water contact angle of the surface. Reaction of 3-(trimethoxysilyl)propyl methacrylate to a hydrophilic surface leads to an increase in the water contact angle. As a control, the contact angles of both unsilanized and silanized plasma-cleaned glass surfaces were measured and were found to be 5° to 63°, respectively.

Before silane-coupling, the grit-blasted samples had a contact angle of 7°. After silane functionalization, the contact angle increased to 14°. In general, the unroughened substrates showed a more dramatic change in hydrophilicity. For instance, the contact angle of the plasma-cleaned $SiO_2$-coated titania increased from 2° to 53° after silanization. An even more pronounced effect was shown on the plasma-cleaned, plain titania, where the contact angle increased from 2° to 82° after silanization. Untreated titania (without plasma cleaning) is already relatively hydrophobic, and there was no change in contact angle with silane coupling. This is most likely because the lack of oxides on the surface of the untreated titanium precluded the silanization from taking place. Thus, in each case (with the exception of the uncleaned titania), there was a change in the water contact angle after silanization, indicating that the silane coupling reactions were successful on the substrate surfaces. The relatively small change in the contact angle between unsilanized and silanized grit-blasted titania is presumed to be related to the roughening of the surface.

Figure 6:
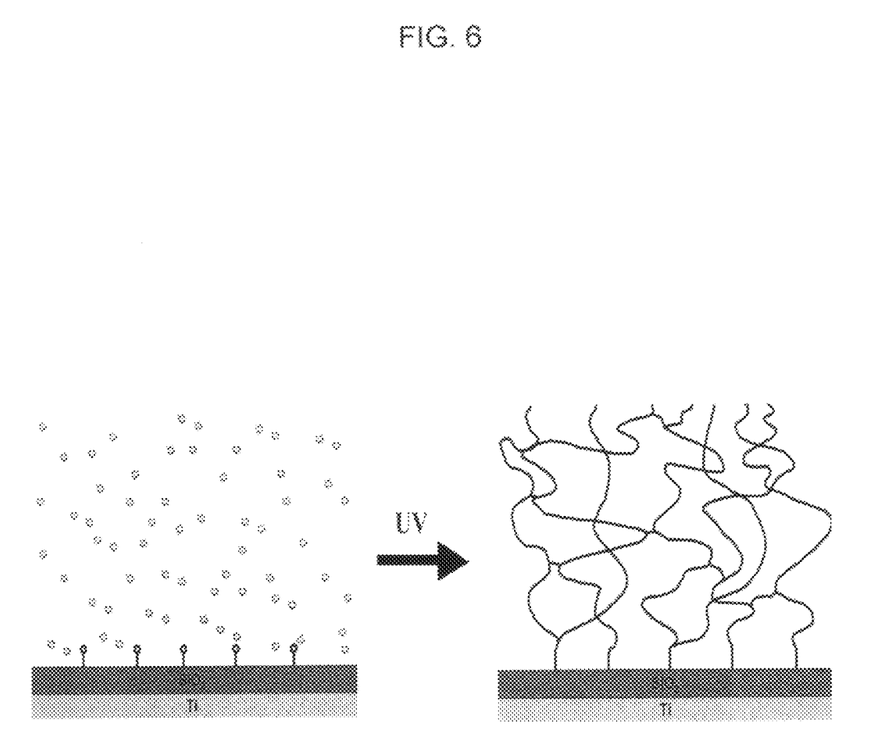
FIG. 6 shows according to an embodiment of the present invention an example of forming a monomer-based single network on a titanium surface, vinyl-based monomer solutions (small circles) are cast over a titanium/$SiO_2$ surface that is functionalized with UV-sensitive crosslinkable groups (small circles), along with photoinitiator and a crosslinking agent (not shown). Exposure to UV light in the presence of a photoinitiator leads to free-radical polymerization and crosslinking of the monomers with each other and with the $SiO_2$ surface. The result of the free-radical polymerization and crosslinking is shown on the right.
Figure 7:
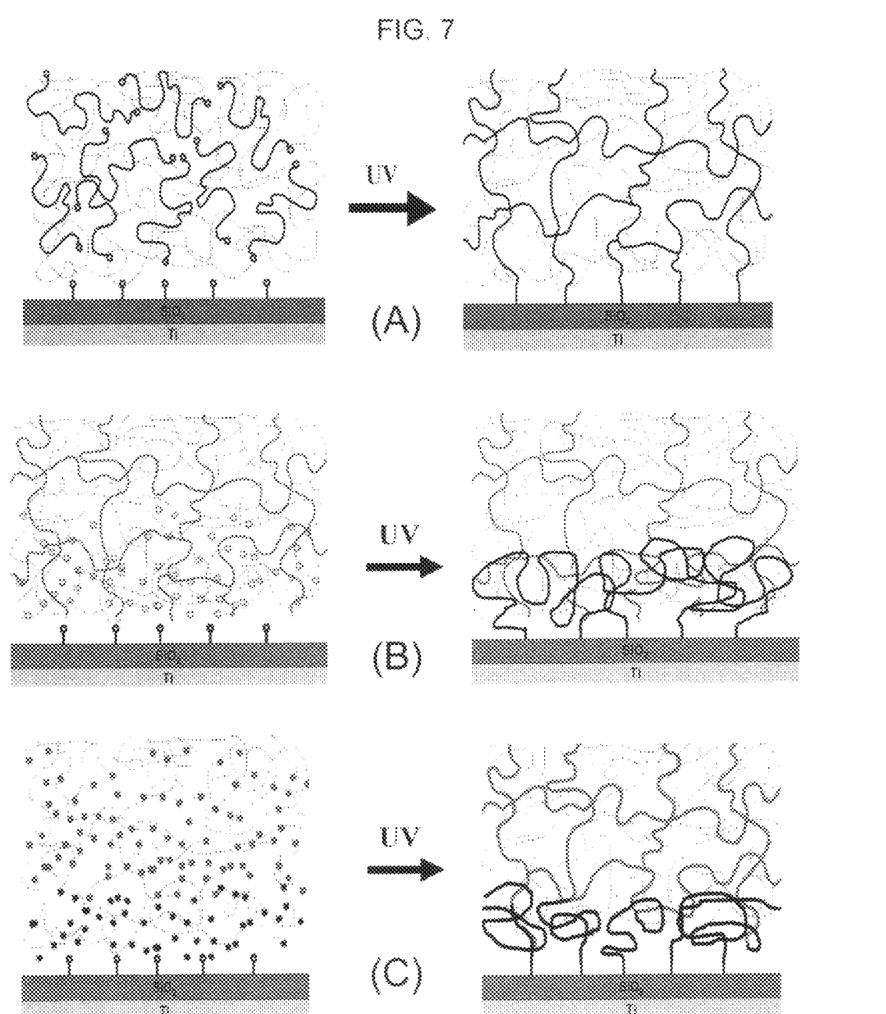
FIG. 7 shows according to an embodiment of the present invention an example of forming interpenetrating polymer networks on the surface of titanium.

Single network hydrogels based on a monomeric precursor were prepared on the surface of the modified titanium. This process is shown in FIG. 6. In addition, semi-interpenetrating polymer networks of PEG and PAA were prepared on the titanium surfaces. A neutral telechelic macromonomer network of PEG-DMA was covalently bonded to the surface of the titanium. Interpenetrating this was a physical network of linear PAA macromonomers of high molecular weight (250,000 Da). Schematics showing the synthesis and bonding of this semi-interpenetrating PEG/PAA network to titanium are shown in FIG. 7(A).

A fully interpenetrating network in which a separate polymer acts as the anchoring intervening polymer network was also grafted to surface-modified titanium (illustrated in FIG. 10(B)). A pre-existing interpenetrating polymer network (thin and thick grey lines) of PEG and PAA was placed over a titanium/$SiO_2$ surface that was functionalized with UV-sensitive crosslinkable groups (small circles). Placed at the interface between the hydrogel and surface-modified metal was a precursor solution of PEG-dimethacrylate macromonomers (grey circles). These macromonomers partially had penetrated the matrix of the overlying interpenetrating polymer network by allowing them to diffuse into the existing IPN (by soaking) for two hours. Upon exposure to UV, the monomers polymerized and crosslinked to the surface-modified titanium, yielding an intervening polymer network that was bonded to the underling surface and entangled with the overlying hydrogel.

In addition to the approaches described above, a fully interpenetrating network in which one of the networks is interfacially copolymerized with an anchoring intervening polymer network can be fabricated according to the present invention. A pre-existing homopolymer network (thin lines) can be placed over a titanium/$SiO_2$ surface that is functionalized with UV-sensitive crosslinkable groups (small circles). The homopolymer network would then be swollen with the precursor monomers of a second network (grey circles). At the interface between the monomer-swollen hydrogel and the surface-modified metal is placed a precursor solution of another reactive monomer (black circles). These monomers partially penetrate the matrix of the overlying interpenetrating polymer network. Upon exposure to UV, the monomers co-polymerize, with the monomers at the interface crosslinking to the surface-modified titanium, yielding an intervening polymer network that is bonded to the underling surface and entangled with the overlying hydrogel.

Exemplary results of three types of hydrogel-metal assemblies are a crosslinked PHEMA homopolymer that has been grafted directly to $SiO_2$-modified titanium, a semi-IPN of PEG-diacrylate and PAA where the PEG network is grafted to the $SiO_2$-modified titanium, or a PEG/PAA IPN that is attached to titanium through an interdiffused, intervening polymer network of PEG-dimethacrylate (molecular weight 1000) grafted to the $SiO_2$ on the titanium. In each of these examples, the water-swollen hydrogel in the photograph is bonded to the titanium on one side by covalent linkages to an intervening layer of $SiO_2$.

PEG(1000)-DMA was cured over the surfaces of all of the silanized surfaces listed in Table 1, with the exception of the plain titania. The samples were left in deionized water overnight to allow the hydrogel to achieve equilibrium swelling. At the precursor concentration of PEG(1000)-DMA that we used, the resultant hydrogel swells about 10% in volume. This isotropic expansion of the hydrogel network is expected to generate stresses at the interface between the hydrogel and underlying substrate to which it is grafted. Therefore, if the bond strength between the hydrogel and the substrate is high, then the hydrogel would be expected to remain bonded to the surface even after equilibrium swelling. On the other hand, if the bond strength is low, then the hydrogel would likely delaminate from the surface. Of all the cases studied, only the grit-blasted surfaces were successful in retaining the hydrogel after swelling to equilibrium. The adhesion strength of the hydrogel-grafted, grit-blasted surfaces was subsequently evaluated by lap-shear adhesion tests.

Strength of Hydrogel Bonding to Titanium

The strength of the chemical bond between exemplary intervening polymers and titanium bonding was tested using lap-shear adhesion experiments in which two titanium plates were adhered together using a thin layer (250 μm) of hydrogel and pulled apart using tensile testing apparatus. Adhesion to both surface-modified titanium (via silyl-methacrylate linkage) and unmodified titanium surfaces (no grit-blasting, plasma, silane, or vapor deposition treatment) was tested. In addition, three different hydrogels were tested: (1) a PEG (1000)-DMA single network, (2) a PHEMA single network, and (3) a PEG/PAA semi-interpenetrating network, all of which would be expected to form bonds with the methacrylate groups on the modified titanium surface. Lap-shear experiments were carried out on phosphate buffer soaked gels as described previously, and the data obtained is shown in FIG. 8.

Figure 8:
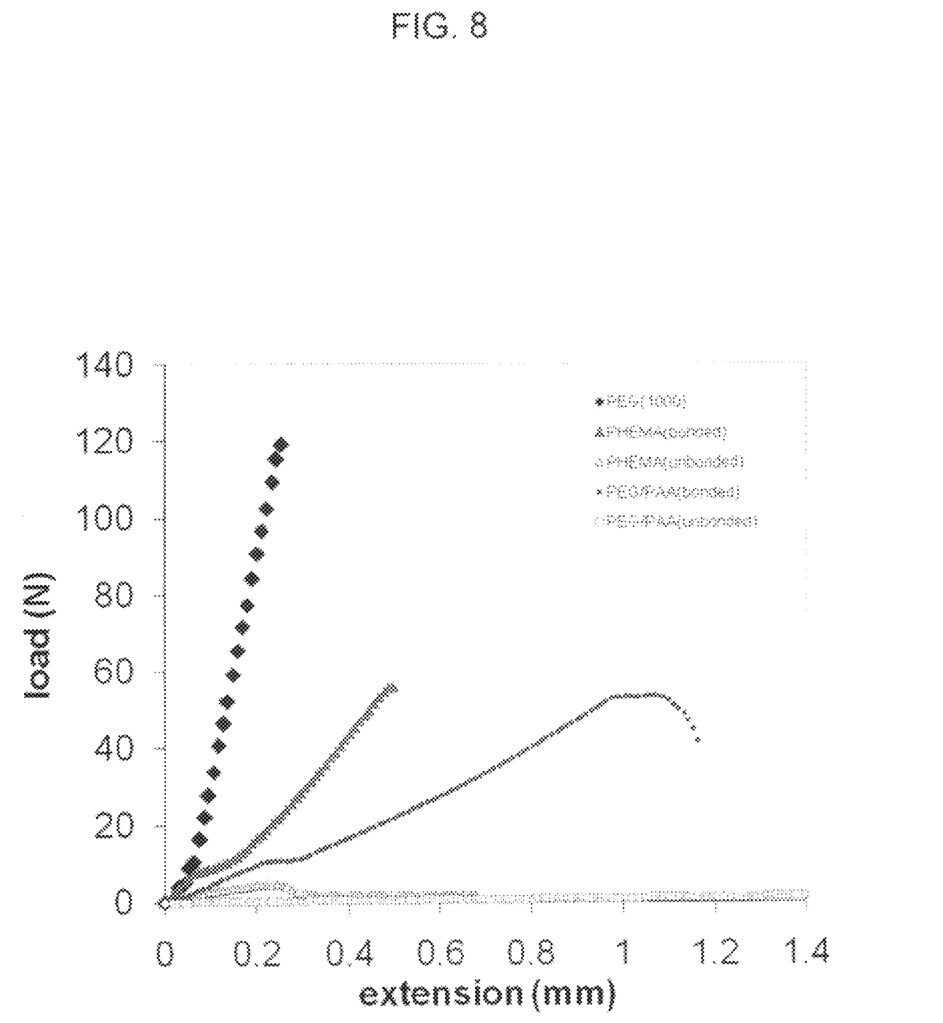
FIG. 8 shows according to an embodiment of the present invention exemplary results of load versus extension data from a lap-shear experiment involving PEG-dimethacrylate (diamonds), PHEMA (triangles), and PEG/PAA semi-IPNs (circles) formed between functionalized titanium (solid shapes) and unfunctionalized titanium (open shapes).

The three types of grafted hydrogels exhibited different bonding strengths. The PEG-DMA hydrogel was the strongest of the three, with a failure load of 120 N, failure stress of 600 kPa, and shear modulus of 1200 kPa. Without silanization of the grit-blasted surface, the PEG-DMA hydrogel did not bind to the titanium and delaminated upon overnight soaking in water. This is likely due to the swelling of the hydrogel, leading to shearing of the hydrogel off of the grit-blasted surface. Similar results were observed for bonding of PHEMA hydrogels to silanized and unsilanized grit-blasted titanium (FIG. 8, triangles). The silane-coupled PHEMA hydrogel failed at a load of 56 N, with a failure stress of 280 kPa and shear modulus of 300 kPa. In the case of PHEMA, however, some adhesion was exhibited between the titanium plates without chemical modification (red open triangles, FIG. 8), and thus a lap-shear experiment could be carried out. This is most likely due to the intrinsically more adhesive or "sticky" surface of the relatively hydrophobic PHEMA hydrogel coupled with the fact that PHEMA exhibits relatively little swelling after polymerization compared to PEG/PAA. The combination of these factors would facilitate a small level of physical adhesion to the adjacent titanium surface.

SEM analysis of the PEG(1000) hydrogel-titanium assembly after lap-shear-induced failure indicated that the failure took place within the bulk of the hydrogel rather than at the hydrogel-$SiO_2$ interface (not shown). SEM analysis of the PHEMA hydrogel-titanium assembly after lap-shear testing indicated a similar result as for PEG(1000) gels (not shown).

In the case of the PEG/PAA semi-IPN bonded to titanium, 53 N of load was required to separate the titanium plates (not shown). This hydrogel exhibited a fracture stress of 260 kPa and a shear modulus of about 125 kPa. In contrast, virtually no load was necessary to pull apart the titanium plates when the titanium was not chemically modified. The hydrogel was easily delaminated from the unmodified titanium surface. This indicates that the tribochemical, silyl-methacrylate surface modification is necessary for strong bonding between the PEG/PAA semi-IPN hydrogel.

Gross inspection of the separated titanium samples indicated (not shown) a stark difference between the chemically bonded and unbonded titanium-hydrogel-titanium "sandwiches." The chemically bonded samples were separated by fracture of the bulk hydrogel, indicated by the hydrogel material left behind on both sides of the titanium sandwich. In contrast, the unmodified titanium-hydrogel-titanium sandwiches were delaminated along the titanium-hydrogel interface (not shown). The lack of bonding between the hydrogel and the titanium, coupled with the swelling of the hydrogel, led to virtually no adhesion between the materials, and ultimate separation into three discrete components (two titanium plates and one hydrogel sheet).

SEM analysis indicated that the failure in the chemically bonded PEG/PAA semi-IPN hydrogel occurred primarily within the bulk of the hydrogel rather than at the hydrogel-$SiO_2$ interface, as fragments of hydrogel are still present on the surface of the titanium (not shown).

CONCLUSION

The results from these experiments indicate that both chemical and physical modifications are required for successful grafting of highly swellable hydrogels to titanium surfaces. This effect was seen in the different surfaces used to bond the PEG-DMA hydrogels (Table 1). Of the various silanized surfaces evaluated, only the grit-blasted titanium was able to retain grafting of the PEG-DMA hydrogels; all of the unroughened silane-coupled surfaces spontaneously failed in water due to swelling of the PEG-DMA network after polymerization. The grit-blasted surfaces were three times rougher than the plain titania and nearly 100 times rougher than glass. Therefore, roughening of the underlying surface greatly increases the strength of the hydrogel graft, most likely due to a great increase in the surface area for chemical adhesion.

While silane-coupling agents enable covalent linkages between certain oxide-containing inorganic substrates and polymers, in the case of hydrogel materials with internal osmotic stresses, shear stresses at the bond interface may make maintenance of adhesion problematic. We have shown that deposition of $SiO_2$ alone is not sufficient for achieving robust adhesion between hydrogels and titania, and that roughening, for example by $SiO_2$-coated alumina particle grit-blasting, is a required element for the adhesion process to succeed. This is not unlike what is seen with the bonding of paint primers to natural or synthetic surfaces, where roughening with sandpaper greatly increases the surface area and subsequent adhesion of the primer prior to applying a paint coat.

We found that the grit-blasting process may not be as homogeneous as specified by the manufacturer of the Rocatec Jr. System. The EDX composition mapping data shows that the grit-blasted surfaces contained roughly equal distributions of $SiO_2$, $Al_2O_3$, and titanium. This result, however, does not necessarily affect the silanization process in a negative manner. Of note, binding of molecules with silane functional groups has been achieved on all three of these materials. Therefore, despite the fact that $SiO_2$ does not form a homogeneous coating on the titanium surface, the silane coupling could conceivably occur over the entire surface regardless of which of the three materials is present. Uniform coverage would only be possible, however, if the reactivity of silanes to each of these surfaces is the same.

As indicated in Table 1, the PEG-DMA grafted to the grit-blasted titanium was successfully retained after post-polymerization equilibrium swelling. This means that the gel matrix and/or the chemical bonds with the grit-blasted titanium are strong enough to withstand the small degree of swelling (10 vol. %) the network exhibits after polymerization. Similarly, PHEMA networks did not delaminate in the long-term, presumably due to lower osmotic pressures inside the gel since the gel does not swell after polymerization. It may also be because of hydrophobic stabilization of the grafted network structure made possible through hydrophobic interaction between the abundant methacrylate groups of PHEMA and the methacrylate groups coupled to the underlying substrate.

As one of ordinary skill in the art will appreciate, various changes, substitutions, and alterations could be made or otherwise implemented without departing from the principles of the present invention. Accordingly, the scope of the invention should be determined by the following claims and their legal equivalents.

The invention claimed is:

1. A hydrogel-metal assembly, comprising:
an intervening polymer network having bonded together the surfaces of a water-swollen hydrogel layer and a biocompatible, surface-modified metallic layer,
wherein said hydrogel layer is an interpenetrating polymer network hydrogel comprising a first network physically entangled with a second network, wherein said first network comprises telechelic macromonomers with diacrylamide as the end groups of said telechelic macromonomers and wherein said second network comprises chemically crosslinked polymers, wherein said intervening polymer network comprises telechelic macromonomers,
wherein said biocompatible surface-modified metallic layer is surface-modified with an inorganic material, and
wherein said intervening polymer network has been chemically grafted to said inorganic material of said biocompatible surface-modified metallic layer through bi-functional linker molecules, and wherein said intervening polymer is physically or chemically cross-linked with said telechelic macromonomers of said water-swollen hydrogel.

2. The hydrogel-metal assembly as set forth in claim 1, wherein the maximum thickness of said hydrogel layer is at least and greater than 0.5 mm.

3. The hydrogel-metal assembly as set forth in claim 1, wherein at least 15% and up to 95% of the volume of said hydrogel layer is a fluid.

4. The hydrogel-metal assembly as set forth in claim 1, wherein the surface coefficient of friction of said hydrogel layer is less than 0.2.

5. The hydrogel-metal assembly as set forth in claim 1, wherein the surface of said biocompatible metallic anchoring layer has a roughness of over 500 nm.

6. The hydrogel-metal assembly as set forth in claim 1, wherein said hydrogel-metal assembly has shear strength of at least 30 kPa.

7. The hydrogel-metal assembly as set forth in claim 1, wherein said hydrogel-metal assembly forms a medical device, medical implant, an artificial implant, an orthopedic implant, or at least as part of a joint.

8. The hydrogel-metal assembly as set forth in claim 1, further comprising an opposing layer wherein the surface of said opposing layer faces the surface of said hydrogel layer, and wherein the two facing layers form a medical device, medical implant, an artificial implant, an orthopedic implant, or at least as part of a joint.

9. The hydrogel-metal assembly as set forth in claim 1, further comprising an opposing layer wherein the surface of said opposing layer comprises metal, ceramic, bone, cartilage, a polymer, a hydrogel, or a water-swollen hydrogel of at least two interpenetrating polymers.

* * * * *